(12) United States Patent
Young et al.

(10) Patent No.: US 11,447,751 B2
(45) Date of Patent: Sep. 20, 2022

(54) METHOD FOR CIRCULATING TUMOR CELLS ISOLATION

(71) Applicant: National Taiwan University, Taipei (TW)

(72) Inventors: Tai-Horng Young, Taipei (TW); Wan-Chen Huang, Taipei (TW); Hao-Ying Hsieh, Taipei (TW); Shyh-Chyi Lo, Taipei (TW); Ke-Cheng Chen, Taipei (TW); Jin-Shing Chen, Taipei (TW); Yin-Tzu Chen, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 417 days.

(21) Appl. No.: 16/560,648

(22) Filed: Sep. 4, 2019

(65) Prior Publication Data
US 2020/0095555 A1 Mar. 26, 2020

(30) Foreign Application Priority Data
Sep. 21, 2018 (TW) ................................. 107133389

(51) Int. Cl.
*C12N 5/09* (2010.01)

(52) U.S. Cl.
CPC ......... *C12N 5/0693* (2013.01); *C12N 5/0694* (2013.01); *C12N 2523/00* (2013.01); *C12N 2533/78* (2013.01)

(58) Field of Classification Search
CPC . C12N 5/0693; C12N 5/0694; C12N 2533/78
See application file for complete search history.

(56) References Cited

U.S. PATENT DOCUMENTS

2011/0244443 A1* 10/2011 van Rijn ............. A61M 1/3403
435/283.1

OTHER PUBLICATIONS

Yu et al., Circulating tumor cells: approaches to isolation and characterization. Journal of Cell Biology, vol. 192, No. 3 (Feb. 7, 2011) pp. 373-382. (Year: 2011).*
Mohamed et al., Isolation of tumor cells using size and deformation. Journal of Chromatography, vol. 47 (Nov. 20, 2009) pp. 8289-8295. (Year: 2009).*

* cited by examiner

*Primary Examiner* — Kara D Johnson
(74) *Attorney, Agent, or Firm* — Chun-Ming Shih; Lanway IPR Services

(57) ABSTRACT

A method of circulating tumor cells isolation, using an isolating cultural system of circulating tumor cells, comprises the following steps: (1) providing a sample; (2) adding a cell culture medium to the isolating cultural system of circulating tumor cells; (3) adding the sample to the isolating cultural system of circulating tumor cells to cultivate; and (4) collecting the suspended circulating tumor cells in the cell culture medium; wherein the isolating cultural system of circulating tumor cells comprises a container including a cell adhesion portion, and cellulose coated on the cell adhesion portion.

5 Claims, 6 Drawing Sheets

METHOD FOR CIRCULATING TUMOR CELLS ISOLATION

CROSS-REFERENCE TO RELATED APPLICATIONS

This application claims the priority of Taiwan Application No. 107133389 filed on Sep. 21, 2018 in the State Intellectual Property Office of the R.O.C., the disclosure of which is incorporated herein by reference.

BACKGROUND OF THE INVENTION

Field of the Invention

The present application relates to a method of circulating tumor cells isolation, and particularly relates to a method for isolating the circulating tumor cells by using a cell cultural container which its cell adhesion portion is coated with cellulose and/or its derivatives.

Descriptions of the Related Art

At present, there are many methods for detecting circulating cancer cells (CTCs), including: cell size isolation method, immune magnetic-activated cell sorting method, density gradient centrifuge method. There are also many subsequent analysis methods, including: Immunofluorescence technique, reverse transcription-polymerase chain reaction, flow cytometry, gene chip, etc. The above methods have their own advantages, but the biggest drawback is the inability to achieve the standardized testing. Due to various factors, such as reagent composition, operation procedure, and interpretation process, the repeated test results of the same sample are prone to deviation. ° Most of the products currently on the market use specific biological antibodies to capture cancer cells in the blood, thereby achieving the function of screening cancer cells. For example: CRC Monitor Intestinal tracking is based on the specific colorectal cancer antigen EpCAM, and the detected cancer cells are isolated by filtration and centrifugation.

For example, the CellSearch system is currently the only CTCs detection technology certified by the US FDA. The main components of the CellSearch system reagent include: epithelial adhesion protein (EpCAM) immunomagnetic strain, cell immobilization reagent, fluorescent labeling reagent, buffer, etc. In the Autoprep system, the corresponding reagents will be automatically added in steps. First, the CTCs are captured by EpCAM. After the enriched cells are fixed, the instrument will automatically add fluorescent antibodies for labeling. The used antibodies with fluorescently labeled include PE-labeled cytokeratin (CK), containing CK8, CK18 and CK19, and APC labeled CD45. In addition, there is DAPI in the reagent, which is specifically used for staining the nucleus. The fixed and stained cells were subjected to four-channel scanning analysis in the Analyzer system. The system will automatically screen for CK-positive events for detection and interpretation, in line with the tumor cell type and "CK, DAPI, CD45 blanks" will be defined as CTCs.

The CellSearch system detects the CTCs by drawing 7.5 ml of blood into a centrifuge tube, adding 6.5 ml of buffer, mixing and centrifuging, and the cells in the blood will settle at the bottom of the centrifuge tube. The sample was put into the Autoprep system, the corresponding parameters were set, the instrument would automatically fix the blood sample, dye, clean, etc. The processed sample is automatically transferred to the MagNest unit, and Leaving it in the dark for more than 20 minutes. The MagNet is placed in the Analyzer system for fluorescence scanning, and the system would perform a preliminary analysis of the scanning results, and finally the personnel will perform the interpretation. The entire detecting process takes about 3-4 hours, so the inspection procedure is cumbersome. The required specific antibodies are expensive, and the detection cost is relatively high.

At present, most of the cancer medical tests use the polymerized chain reaction (PCR) as a tool for interpretation. In the process of detection, white blood cells and red blood cells in the blood are often prone to false positives in the interpretation results. Hence, how to separate the blood cells from the cancer cells in the detection system is the biggest challenge.

SUMMARY OF THE INVENTION

In view of the problems existing in the prior art, the present application provides a method of circulating tumor cells isolation, using an isolating cultural system of circulating tumor cells, comprises the following steps:

(1) providing a sample,
(2) adding a cell culture medium to the isolating cultural system of circulating tumor cells,
(3) adding the sample to the isolating cultural system of circulating tumor cells to cultivate, and
(4) collecting the suspended circulating tumor cells in the cell culture medium, wherein the isolating cultural system of circulating tumor cells comprises a container including a cell adhesion portion, and cellulose and/or its derivatives coated on the cell adhesion portion.

In an embodiment, the coated amount of the cellulose and/or its derivatives on the cell adhesion portion is 3-20 $mg/cm^2$. Preferably, the coated amount on the cell adhesion portion is 6-15 $mg/cm^2$. More preferably, the coated amount on the cell adhesion portion is 12-13 $mg/cm^2$.

In an embodiment, the sample is a blood sample.

In an embodiment, the cellulose derivative is methyl cellulose and/or carboxymethyl cellulose.

In addition, the present application further provides a method for preparing an isolating cultural system of circulating tumor cells, comprises the following steps:

(1) dissolving cellulose and/or its derivatives into a solution,
(2) placing the solution at a temperature below the freezing point until completely frozen,
(3) thawing the frozen solution,
(4) repeating steps (2) and (3) until the solution being translucent,
(5) adding the translucent solution into a container, wherein the solution covers a cell adhesion portion of the container, and
(6) drying the solution of step (5) in the shade to a solid state.

In an embodiment, the container is dried in the shade by placing at 20° C.-35° C. and humidity 30%-55% in step (6).

In an embodiment, the solution is placed at 0° C.-30° C. for 2-6 hours in step (2), and the solution is thawed by placing at room temperature in step (3).

The present application utilizes the special affinity difference of cellulose and/or its derivatives for different cells to achieve the effect of isolating tumor cells from the blood sample. Cellulose and/or its derivatives themselves have the characteristic that to let the white blood cells in the blood adhere to it. The present application further discloses that the white blood cells are adhered to the cellulose and/or its derivatives but the cancer cells are suspended in the culture medium after a blood sample to be tested culturing on a cell cultural container which its cell adhesion portion is coated with cellulose and/or its derivatives. After the blood containing cancer cells being cultured in the cellulose and/or its derivatives coated-cell cultural container for a period of time, the red blood cells would settle at the bottom, the white blood cells would adhere to the cellulose and/or its derivatives, and the cancer cells would suspend in the culture medium, which achieves the effect of separating cancer cells from the blood. The cancer cells can further be isolated from the cultural system for related analysis and detection to achieve early diagnosis and screening. This isolation process does not use specific biological antibodies. Compare with other products, therefore, the operation is relatively simple, convenient, time-saving and low-cost.

The details of the invention are set forth in the following description, which is to be regarded as illustrative methods and materials only, and not restrictive. Other similar or equivalent methods and materials described herein to practice or test the present invention should be regarded as the scope of the resent application. In the specification and the appended claims, the singular form includes the plural as well unless the context clearly indicates otherwise. Unless otherwise defined, all technical and scientific terms used herein have the same meaning as generally understood as one having ordinary skill in the art of the present invention.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
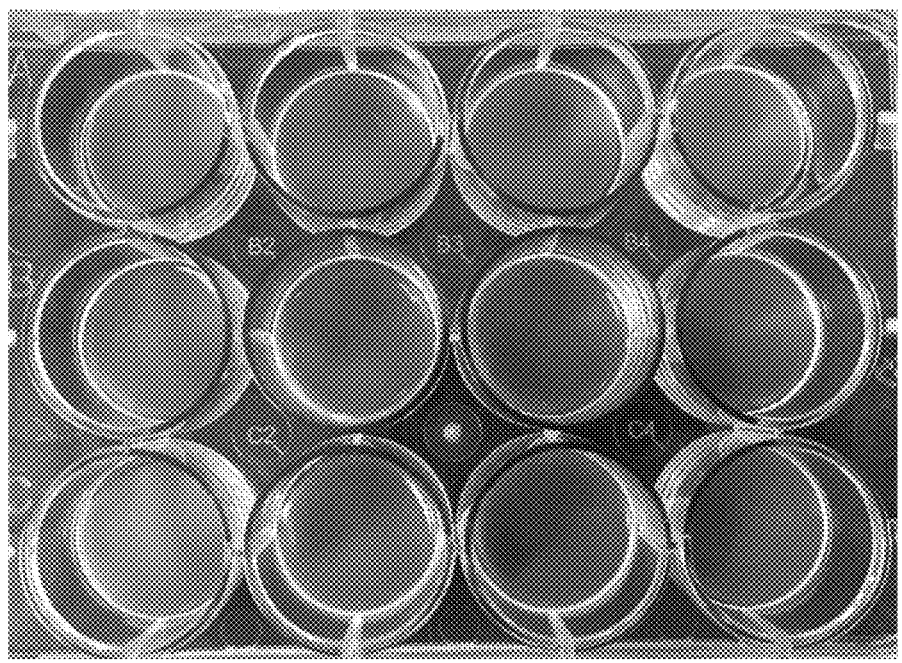
FIG. 1 shows the isolating cultural system of circulating tumor cells of the present application.

Reference will be made in detail description to the exemplary embodiments and drawings for being more readily understood to the advantages and features of the present invention, as well as the methods of attaining them. However, the present invention may be carried out in many different forms and should not be construed as limited to the embodiments set forth herein. Conversely, these embodiments are provided to render the present disclosure to be conveyed the scope of the present invention more thoroughly, completely, and fully to one having ordinary skill in the art of the present invention. Moreover, the present invention would be defined only by the appended claims. As used herein, the term "and/or" includes any and all combinations of one or more of the associated listed components.

Unless otherwise defined, all terms (including technical and scientific terms) used herein have the same meaning as generally understood by one having ordinary skill in the art of the present invention. It will be more understandable that, for example, the terms defined in commonly used dictionaries should be understood to have meanings consistent with the contents of the relevant fields, and would not be interpreted overly idealized or overly formal unless clearly defined herein. As described in the present specification, a range of values is used as a shorthand to describe each and every numerical value in the range, and any number within that range may be chosen as the end-value of that range.

As used herein, the term "circulating tumor cells" refers to the cancer cells that are shed from the original tumor and circulate in the bloodstream. The detection of circulating tumor cells can be used as a rapid assessment of the in vivo efficacy of chemotherapy drugs, determination of the prognosis and survival duration of patients, monitoring and timely diagnosis of tumor relapse in patient, in vitro drug screening of tumor individualized treatment, and early diagnosis of tumor, etc. In addition to clinical applications, circulating tumor cells can also be used in basic research of many pharmaceutical companies and research institutions, including the search for new tumor markers and the development of new anti-tumor drugs.

As used herein, the term "cell adhesion portion" refers to the bottom, the side wall, or any portion of the cell cultural container that cells can contact and adhere to grow.

The present application provides a method of circulating tumor cells isolation, using an isolating cultural system of circulating tumor cells, comprises the following steps:

(1) providing a sample, (2) adding a cell culture medium to the isolating cultural system of circulating tumor cells, (3) adding the sample to the isolating cultural system of circulating tumor cells to cultivate, and (4) collecting the suspended circulating tumor cells in the cell culture medium, wherein the isolating cultural system of circulating tumor cells comprises a container including a cell adhesion portion, and cellulose and/or its derivatives coated on the cell adhesion portion.

In an embodiment, the coated amount of the cellulose and/or its derivatives on the cell adhesion portion is 3-20 mg/cm$^2$. Preferably, the coated amount on the cell adhesion portion is 6-15 mg/cm$^2$. More preferably, the coated amount on the cell adhesion portion is 12-13 mg/cm$^2$.

In an embodiment, the sample is a blood sample.

In an embodiment, the cellulose derivative is methyl cellulose and/or carboxymethyl cellulose.

In addition, the present application further provides a method for preparing an isolating cultural system of circulating tumor cells, comprises the following steps:

(1) dissolving cellulose and/or its derivatives into a solution, (2) placing the solution at a temperature below the freezing point until completely frozen, (3) thawing the frozen solution, (4) repeating steps (2) and (3) until the solution being translucent, (5) adding the translucent solution into a container, wherein the solution covers a cell adhesion portion of the container, and (6) drying the solution of step (5) in the shade to a solid state.

In an embodiment, the container is dried in the shade by placing at 20° C.-35° C. and humidity 30%-55% in step (6).

In an embodiment, the solution is placed at 0° C.-30° C. for 2-6 hours in step (2), and the solution is thawed by placing at room temperature in step (3).

The following examples will illustrate the preparation method of the isolating cultural system of circulating tumor cells provided by the present application, and the experiment procedure and results of the method of circulating tumor cells isolation. The test results are shown in FIG. 1 to FIG. 6; however, the test results of the examples are merely illustrative and are not intended to limit the scope of the present invention.

Example 1—Preparation of the Isolating Cultural System of Circulating Tumor Cells 5 grams of cellulose and/or its derivatives were poured into 100 ml of 5% NaOH. After stirring evenly, the solution is placed at −20° C. for 4 hours to reach complete frozen. Then, the frozen solution was placed at room temperature until completely thawed and was stirred. The freezing-thawing procedures were repeated 5 times until the cellulose solution became translucent. The solution was coated on the culture container in an amount of 12-13 mg/cm$^2$ of cellulose. The coated container was placed at room temperature 26.8-32.6° C., humidity 34.2-52.1%. After drying in the shade for 24 hours, the solid state of the cellulose is gelatinous or jelly-like as shown in FIG. 1. 1 ml of 0.5M HCl was dropped into the coated container and leaving it for 5 minutes. After that, HCl was poured off and the culture container was rinsed twice with filtered water. After sterilization of UV light exposure for 30 minutes, it can be used for culture.

Any conventional or commercially available cellulose and/or its derivatives can be used. This application utilizes Sigma-310697 cellulose as an example, but is not limited thereto.

Example 2—White Blood Cells Adhesion Test 200 ml of whole blood was taken and was centrifuged at 40 rpm for 20 minutes. The upper layer of the plasma was aspirated off, the buffy coat was obtained, and RBC lysis buffer was added to make the volume ratio 1:3. After uniformly mixing, centrifuge at 15 rpm for 5 minutes and aspirate the supernatant. Saline was added and was mixed well, then centrifuge at 15 rpm for 5 minutes again. The obtained white blood cells were equally divided and cultured in a 10 cm dish, which coated with 12-13 mg/cm$^2$ of Chitosan G214, 6-7 mg/cm$^2$ of PMMA, and 6-7 mg/cm$^2$ of cellulose. The culture dish was placed in 5% $CO_2$ incubator at 37 for 2 hours. After that, supernatant was collected and the number of white blood cells which not adhered to the material was calculated through an automated hematology analyzer. The adhesion ratio of blood cells on the material can be obtained by the following formula:

Adhesion ratio of white blood cells (%)=[(Total number of white blood cells before culture−Total number of white blood cells in the supernatant)/Total number of white blood cells before culture]×100

Figure 2:
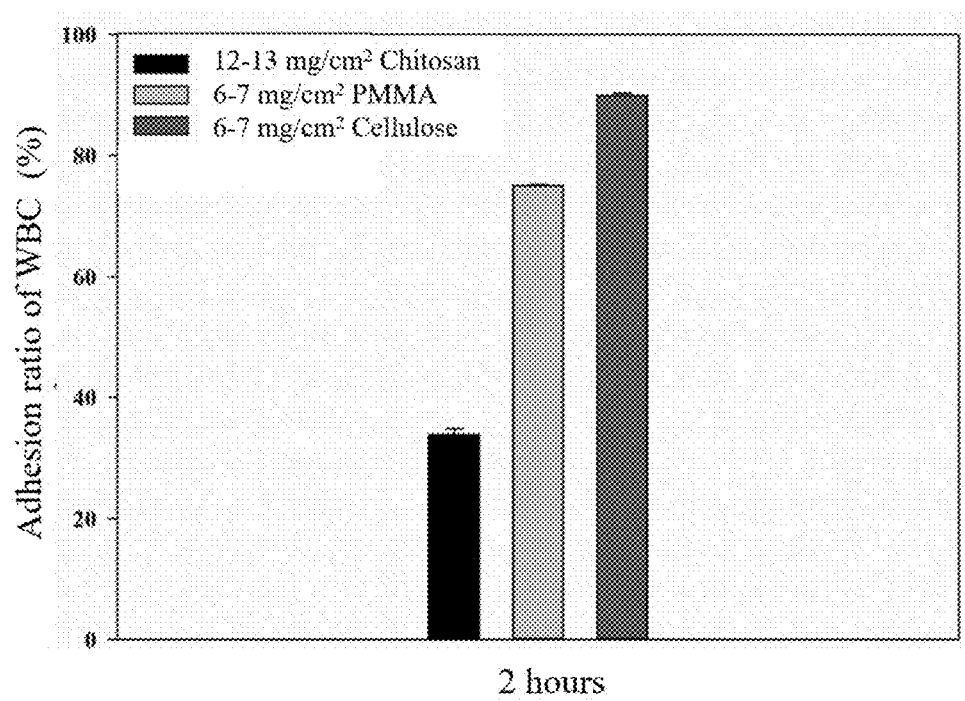
FIG. 2 shows a result of the white blood cell adhesion test.

As can be seen in FIG. 2 that the best effect among the 3 materials is the culture dish coated with 6-7 mg/cm$^2$ of cellulose, which 89.9% of the white blood cells adhere to it. While collecting the supernatant after culturing for 2 hours, however, it was found that the cellulose at the bottom of the culture dish was damaged, which meant that the material was not mechanically strong enough. Therefore, the coated amount of cellulose is further increased and other cellulose derivatives, such as methyl cellulose and carboxymethyl cellulose, are added. The results are shown in FIG. 3.

Figure 3:
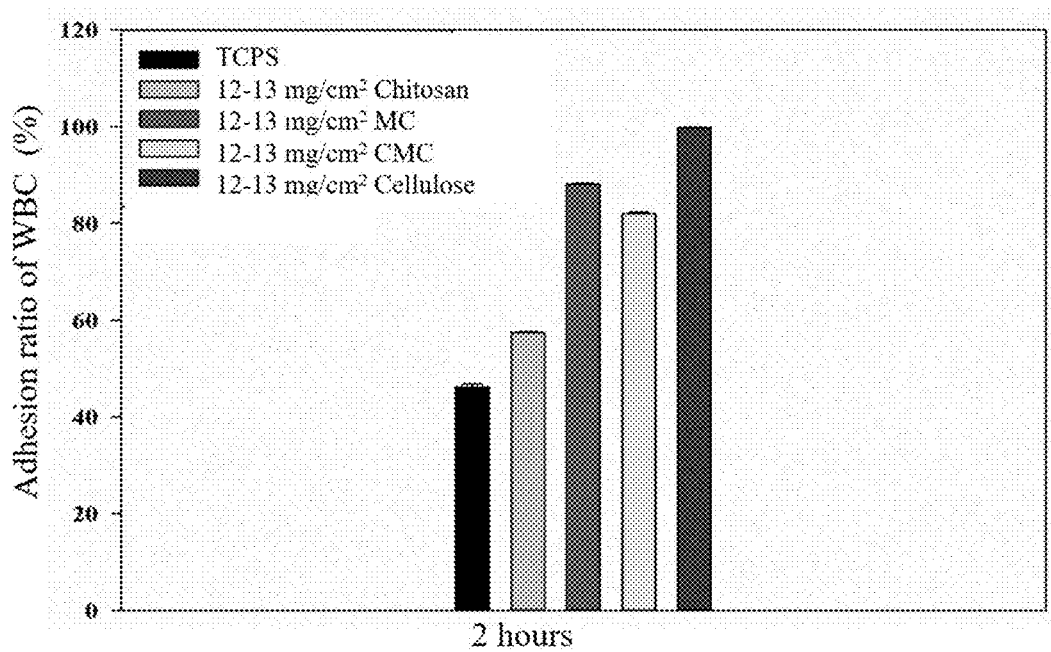
FIG. 3 shows a result of the white blood cell adhesion test.

As can be seen in FIG. 3 that the best effect among the 5 materials is the culture dish coated with 12-13 mg/cm$^2$ of cellulose, which 99.8% of the white blood cells adhere to it. Since the coated amount of cellulose is increased, the mechanical strength of the material is enhanced. The cellulose at the bottom of the culture dish is no longer damaged. Besides, 80%-90% of the white blood cells adhere to the culture dish coated with 12-13 mg/cm$^2$ of methyl cellulose and carboxymethyl cellulose, which also shows a good effect.

Example 3—Tumor Cells Adhesion Test $2×10^4$ of fluorescently labeled cells of A549 (human lung adenocarcinoma cells), HT29 (human colon cancer cells) and HeLa (human cervical cancer cells), were separately provided and cultured on TCPS, the culture container coated with 12-13 mg/cm$^2$ of methyl cellulose+cellulose (40:1), the culture container coated with 12-13 mg/cm$^2$ of cellulose for 2 hours.

Figure 4A:
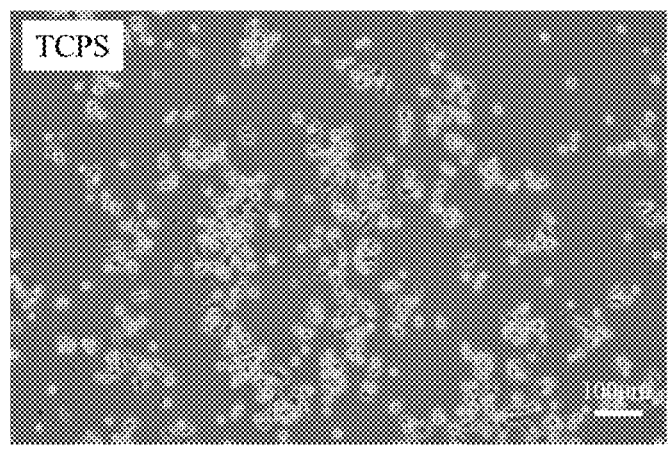
FIG. 4A shows a result of A549 cells cultured on TCPS.
Figure 4B:
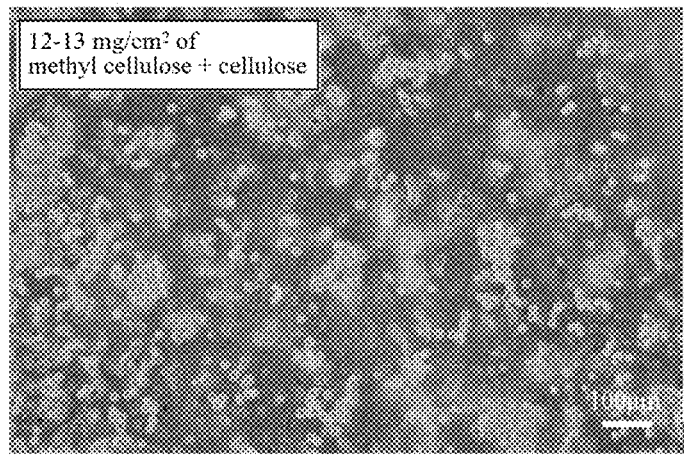
FIG. 4B shows a result of A549 cells cultured on a cell culture dish which coated with 12-13 mg/cm$^2$ of methyl cellulose+cellulose (40:1).
Figure 4C:
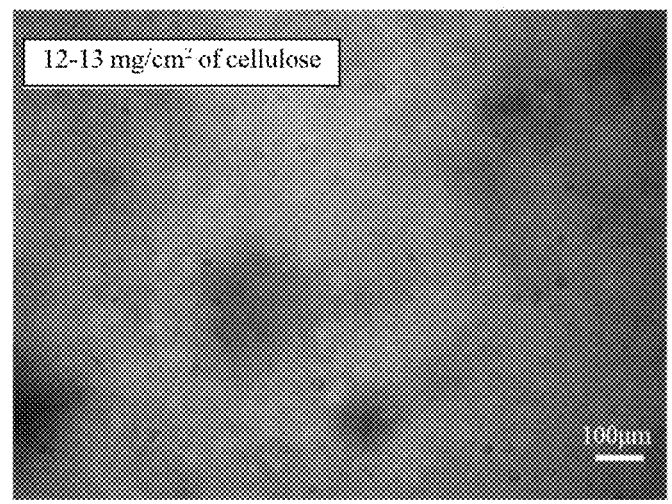
FIG. 4C shows a result of A549 cells cultured on a cell culture dish which coated with 12-13 mg/cm$^2$ of cellulose.

FIGS. 4A-4C are the results of A549 human lung adenocarcinoma cells cultured on different materials. FIG. 4A clearly shows that the A549 cells adhere to TCPS. FIG. 4B shows that the A549 cells are suspended in the culture medium within the cell culture container coated with 12-13 mg/cm$^2$ of methyl cellulose+cellulose (40:1). FIG. 4C shows that the A549 cells are also suspended in the culture medium within the cell culture container coated with 12-13 mg/cm$^2$ of cellulose.

Figure 5A:
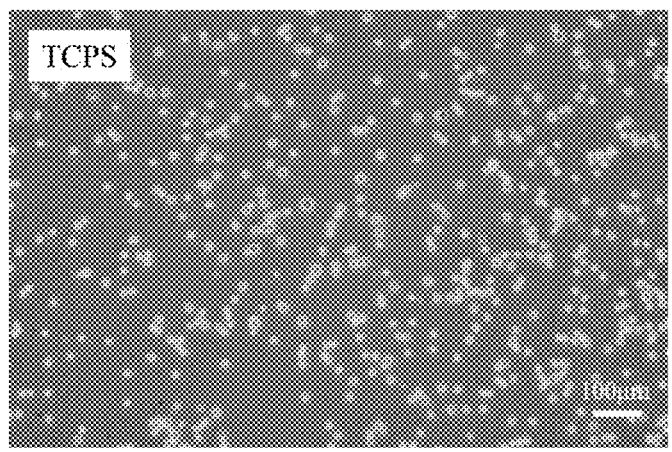
FIG. 5A shows a result of HT29 cells cultured on TCPS.
Figure 5B:
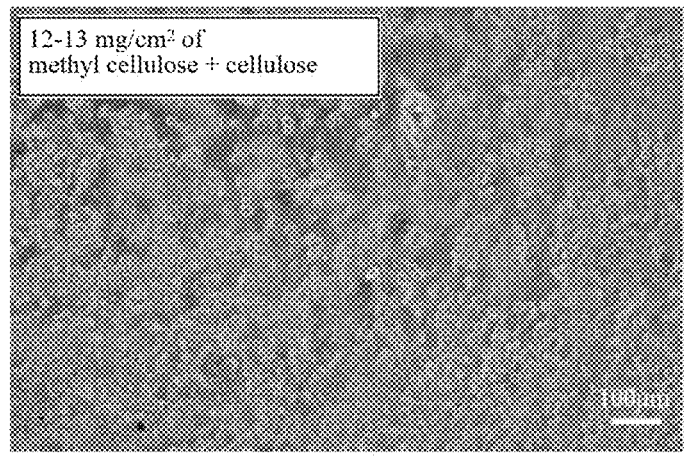
FIG. 5B shows a result of HT29 cells cultured on a cell culture dish which coated with 12-13 mg/cm$^2$ of methyl cellulose+cellulose (40:1).
Figure 5C:
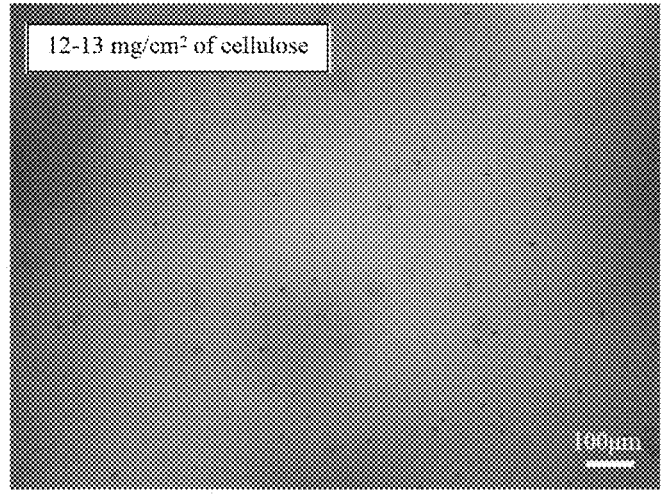
FIG. 5C shows a result of HT29 cells cultured on a cell culture dish which coated with 12-13 mg/cm$^2$ of cellulose.

FIGS. 5A-5C are the results of HT29 human colon cancer cells cultured on different materials. FIG. 5A clearly shows that the HT29 cells adhere to TCPS. FIG. 5B shows that most of the HT29 cells are suspended in the culture medium within the cell culture container coated with 12-13 mg/cm$^2$ of methyl cellulose+cellulose (40:1), but a few of the HT29 cells adhere to the bottom. FIG. 5C shows most of the HT29 cells are suspended in the culture medium within the cell culture container coated with 12-13 mg/cm$^2$ of cellulose, but a few of the HT29 cells adhere to the bottom too.

Figure 6A:
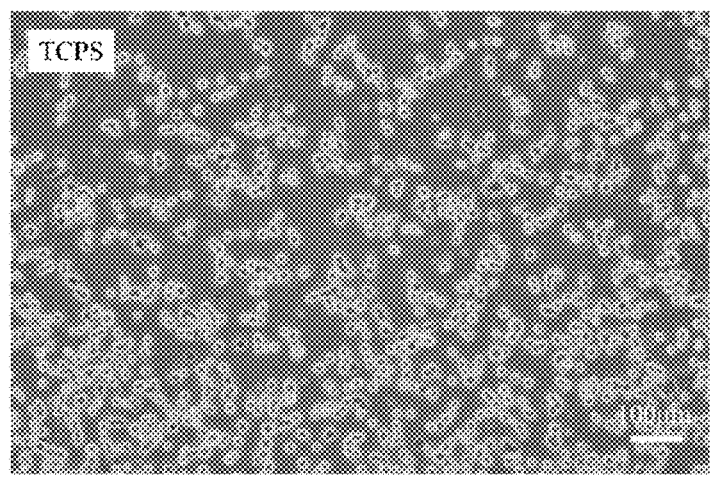
FIG. 6A shows a result of HeLa cells cultured on TCPS.
Figure 6B:
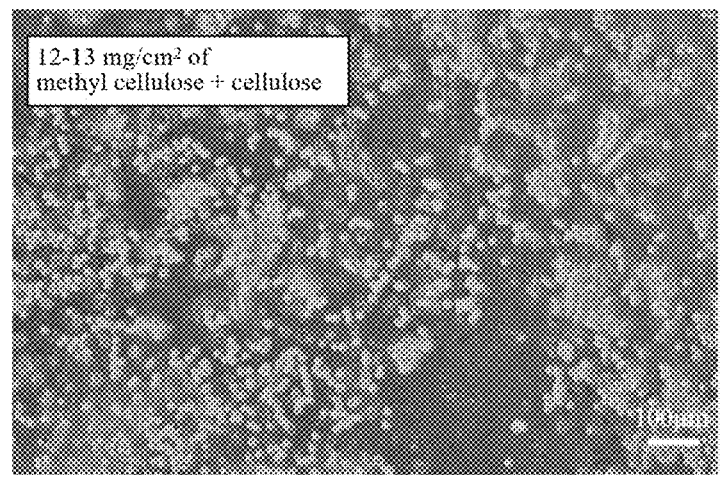
FIG. 6B shows a result of HeLa cells cultured on a cell culture dish which coated with 12-13 mg/cm$^2$ of methyl cellulose+cellulose (40:1).
Figure 6C:
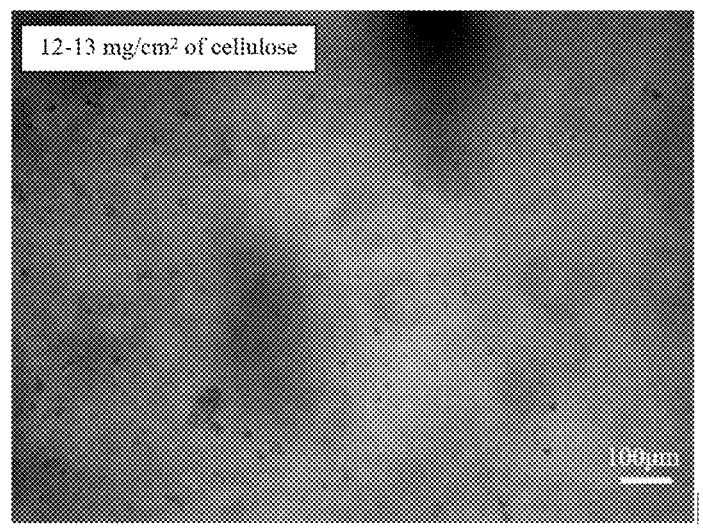
FIG. 6C shows a result of HeLa cells cultured on a cell culture dish which coated with 12-13 mg/cm$^2$ of cellulose.

FIGS. 6A-6C are the results of HeLa human cervical cancer cells cultured on different materials. FIG. 6A clearly shows that the HeLa cells adhere to TCPS. FIG. 5B shows that most of the HeLa cells are suspended in the culture medium within the cell culture container coated with 12-13 mg/cm$^2$ of methyl cellulose+cellulose (40:1), but a few of the HeLa cells adhere to the bottom. FIG. 6C shows most of the HeLa cells are suspended in the culture medium within the cell culture container coated with 12-13 mg/cm$^2$ of cellulose, but a few of the HeLa cells adhere to the bottom too.

From the above results, it is known that cancer cells have a poor affinity to cellulose and/or its derivatives. Most of the cancer cells didn't adhere to the bottom of the culture dish when cultured in cell culture dishes coated with cellulose and/or its derivatives. Instead, the cancer cells were suspended in the cell culture medium, especially the lung cancer cells have the best effect.

Example 4—Test of Circulating Tumor Cells Isolation

From the results of the foregoing Examples 2 and 3, it is understood that cellulose and/or its derivative would let the white blood cells adhere but not for the cancer cells. The present application is based on this characteristic to perform an experiment for circulating tumor cells isolation.

20 μl of whole blood containing anticoagulant CPDA was obtained. 100 fluorescently labeled A549 human lung adenocarcinoma cells were added, and the whole blood containing cancer cells were separately added to a 12-well dish coated with 12-13 mg/cm$^2$ of methyl cellulose+cellulose (40:1) and 12-13 mg/cm$^2$ of cellulose. Each well contained 2 ml of DMEM+10% FBS medium. The culture dish was placed in a 5% $CO_2$ incubator at 37° C. The supernatant was aspirated after culturing for 2 hours.

The aspirated supernatant was added to a 24-well TCPS again. The culture dish was placed in a 5% $CO_2$ incubator at 37° C. After culturing for 4 hours, the number of the cells which adhered to the bottom of the culture dish was observed and calculated through a fluorescence microscope. The isolation ratio of the tumor cells is calculated by the counting results with the following formula:

Isolation ratio of cells (%)=(cell count/100)×100

The counting results and the isolation ratio of the tumor cells are shown in Table 1 below:

TABLE 1

|  | Isolation ratio of cells (%) | Mean ± SD (%) |
| --- | --- | --- |
| Coated with 12-13 mg/cm$^2$ of cellulose (n = 100) | 69<br>75<br>73 | 72.3 ± 2.5% |
| Coated with 12-13 mg/cm$^2$ of methyl cellulose + cellulose (40:1) (n = 100) | 51<br>58<br>56 | 51.7 ± 3.3% |

In addition, another experiment for the isolation of non-fluorescently labeled cancer cells from blood was performed, which simulated the detection process after obtaining CTC-containing blood from the patient.

20 μl of whole blood containing anticoagulant CPDA was obtained. 100 A549 human lung adenocarcinoma cells were added, and the whole blood containing cancer cells were separately added to a 12-well dish coated with 12-13 mg/cm$^2$ of cellulose. Each well contained 2 ml of DMEM+10% FBS medium. The culture dish was placed in a 5% $CO_2$ incubator at 37° C. The supernatant was aspirated after culturing for 2 hours.

The aspirated supernatant was added to a 24-well TCPS again. The culture dish was placed in a 5% $CO_2$ incubator at 37° C. After culturing for 4 hours, the cells were fixed and identified by immunofluorescence staining with CD29 and DAPI. The number of the cells which adhered to the bottom of the culture dish was counted, and the isolation ratio of cells was calculated based on the counting results, which is shown in Table 2 below:

TABLE 2

|  | Isolation ratio of cells (%) | Mean ± SD (%) |
| --- | --- | --- |
| Coated with 12-13 mg/cm$^2$ of cellulose (n = 100) | 69<br>67<br>75 | 70.3 ± 3.4% |

Example 5—Cells Isolation Test of the Coated Amount of Cellulose and/or its Derivatives Whole blood containing anticoagulant CPDA was diluted with 3 ml of PBS in the test group, and the control group was 3 ml of PBS. Both groups were placed in a 12-well dish with different CMC coated amounts. The culture dish was placed in an air-conditioned room at 24-26° C. for 2 hours. The supernatant was collected and the number of white blood cells which not adhered to the material was calculated through an automated hematology analyzer. The adhesion ratio of blood cells on the material can be obtained by the following formula:

Adhesion ratio of white blood cells (%)=[Total number of white blood cells before culture−(Total number of white blood cells in the supernatant−Total number of white blood cells in the control group)/Total number of white blood cells before culture]×100

The tested adhesion ratio of white blood cells is shown in Table 3 below:

TABLE 3

| Amount of Blood (μL) | Coated amount of CMC (mg/cm$^2$) | Adhesion ratio of WBC (%) Mean ± SD |
| --- | --- | --- |
| 10 | 13 | 100 |
|  |  | 100 |
|  | 6.5 | 100 |
|  | 1.3 | 100 |
| 200 | 6.5 | 73.67 ± 7.00 |
|  | 1.3 | 48.00 ± 7.00 |
| 100 | 13 | 83.70 ± 0.74 |
|  | 13 | 90.37 ± 0.74 |
|  | 13 | 97.78 |

In addition, whole blood containing anticoagulant CPDA was obtained. 1000 fluorescently labeled A549 human lung adenocarcinoma cells were added. The whole blood containing cancer cells were diluted by adding 3 ml dilution, then separately added to a 12-well dish coated with different amount of carboxymethyl cellulose. The culture dish was placed in an air-conditioned room at 24-26° C. for 2 hours. The supernatant was aspirated and added to a 6-well TCPS again. The culture dish was placed in a 5% $CO_2$ incubator at 37° C. After culturing for 5 hours, the number of the cells which adhered to the bottom of the culture dish was observed and calculated through a fluorescence microscope. The isolation ratio of the tumor cells is calculated by the counting results with the following formula:

Isolation ratio of cells (%)=(cell count/1000)×100

The tested isolation ratio of the tumor cells is shown in Table 4 below:

TABLE 4

| Amount of Blood (μL) | Coated amount of CMC (mg/cm$^2$) | Isolation ratio of tumor cells (%) Mean ± SD |
|---|---|---|
| 1 | 13 | 84.73 ± 2.64 |
|   |    | 55.13 ± 5.14 |
| 3 | 13 | 81.07 ± 1.96 |
|   | 6.5 | 79.86 ± 2.26 |
|   | 5.2 | 74.48 ± 1.55 |
|   | 2.6 | 69.70 ± 4.42 |
|   | 1.3 | 29.87 ± 2.96 |

Through the test results of the present application, it was found that the white blood cells cultured in a cellulose-coated culture dish can achieve an adhesion ratio of 99.8%. For the culture of cancer cells (such as A549 lung adenocarcinoma cells, HT29 colon cancer cells, HeLa human cervical cancer cells, etc.), using the culture dish coated with cellulose and/or its derivative have the effect of suspending the cancer cells in the culture medium. It is found that the blood cells are sedimented or adhered to the cellulose and/or its derivative and the cancer cells are suspended in the culture medium if the blood containing cancer cells is cultured in a culture dish coated with cellulose and/or its derivative. Thereby, more than about 70% of the isolation ratio of cancer cells can be obtained without using the specific biological antibodies in the isolation process. Compare with other products, therefore, the operation is relatively simple, convenient, time-saving and low-cost.

The examples above are only illustrative to explain principles and effects of the invention, but not to limit the invention. It will be apparent to those skilled in the art that modifications and variations can be made without departing from the scope of the invention. Therefore, the protection range of the rights of the invention should be as defined by the appended claims.

What is claimed is:

1. A method of circulating tumor cells isolation, using an isolating cultural system of circulating tumor cells, comprises the following steps:
   (1) providing a sample,
   (2) adding a cell culture medium to the isolating cultural system of circulating tumor cells,
   (3) adding the sample to the isolating cultural system of circulating tumor cells and cultivating the sample, and
   (4) collecting suspended circulating tumor cells in the cell culture medium,
   wherein the isolating cultural system of circulating tumor cells comprises a container including a cell adhesion portion, and cellulose and/or its derivatives coated on the cell adhesion portion.

2. The method of claim 1, wherein the coated amount of the cellulose and/or its derivatives on the cell adhesion portion of the isolating cultural system of circulating tumor cells is 3-20 mg/cm$^2$.

3. The method of claim 1, wherein the coated amount of the cellulose and/or its derivatives on the cell adhesion portion of the isolating cultural system of circulating tumor cells is 6-15 mg/cm$^2$.

4. The method of claim 1, wherein the coated amount of the cellulose and/or its derivatives on the cell adhesion portion of the isolating cultural system of circulating tumor cells is 12-13 mg/cm$^2$.

5. The method of claim 1, wherein the sample is a blood sample, the cellulose derivative is methyl cellulose and/or carboxymethyl cellulose.

* * * * *